(12) United States Patent
Jiang

(10) Patent No.: US 10,494,569 B2
(45) Date of Patent: *Dec. 3, 2019

(54) LIQUID CRYSTAL COMPOUND CONTAINING DIFLUOROMETHOXY BRIDGE, COMPOSITION AND APPLICATION THEREOF

(71) Applicants: BEIJING BAYI SPACE LCD TECHNOLOGY CO., LTD., Beijing (CN); DONGJIN SEMICHEM CO., LTD., Incheon (KR)

(72) Inventor: Zhanying Jiang, Shaoxing (CN)

(73) Assignees: BEIJING BAYI SPACE LCD TECHNOLOGY CO., LTD, Beijing (CN); DONGJIN SEMICHEM CO., LTD., Seo-gu, Incheon (KR)

( * ) Notice: Subject to any disclaimer, the term of this patent is extended or adjusted under 35 U.S.C. 154(b) by 36 days.

This patent is subject to a terminal disclaimer.

(21) Appl. No.: 15/521,210

(22) PCT Filed: Jun. 1, 2015

(86) PCT No.: PCT/CN2015/080515
§ 371 (c)(1),
(2) Date: Apr. 21, 2017

(87) PCT Pub. No.: WO2016/082510
PCT Pub. Date: Jun. 2, 2016

(65) Prior Publication Data
US 2017/0349830 A1  Dec. 7, 2017

(30) Foreign Application Priority Data
Nov. 27, 2014  (CN) .......................... 2014 1 0707262

(51) Int. Cl.
| C09K 19/42 | (2006.01) |
| C09K 19/34 | (2006.01) |
| C09K 19/04 | (2006.01) |
| C07D 319/06 | (2006.01) |
| C09K 19/30 | (2006.01) |

(52) U.S. Cl.
CPC ........ *C09K 19/3402* (2013.01); *C07D 319/06* (2013.01); *C09K 19/0403* (2013.01); *C09K 19/3003* (2013.01); *C09K 2019/0466* (2013.01); *C09K 2019/301* (2013.01); *C09K 2019/3004* (2013.01); *C09K 2019/3016* (2013.01); *C09K 2019/3422* (2013.01)

(58) Field of Classification Search
CPC ............................................. C09K 2019/0466
See application file for complete search history.

(56) References Cited

U.S. PATENT DOCUMENTS

| 5,045,229 A | 9/1991 | Batmann et al. |
| 7,291,367 B2 | 11/2007 | Kirsh et al. |
| 8,197,709 B2 | 6/2012 | Lietzan et al. |
| 8,211,513 B2 | 7/2012 | Jansen et al. |
| 2006/6061699 | 3/2006 | Kirsh et al. |
| 2016/0304783 A1* | 10/2016 | Kim .................. C09K 19/0403 |

FOREIGN PATENT DOCUMENTS

| CN | 1182085 A | 5/1998 |
| CN | 101294079 A | 10/2008 |
| CN | 102050708 A | 5/2011 |
| CN | 102199139 A | 9/2011 |
| CN | 102559202 A | 7/2012 |
| CN | 103937508 A | 7/2014 |
| CN | 104031654 A | 9/2014 |
| CN | 104099105 A | 10/2014 |
| CN | 104449761 A | 3/2015 |
| CN | 104498053 A | 4/2015 |
| CN | 104498053 B | 5/2016 |

(Continued)

OTHER PUBLICATIONS

International Search Report (in English and Japanese) and Written Opinion of the International Searching Authority (in Japanese) issued in PCT/CN2015/080515, dated Aug. 26, 2015; ISA/CN.

(Continued)

*Primary Examiner* — Chanceity N Robinson
(74) *Attorney, Agent, or Firm* — Harness, Dickey & Pierce, P.L.C.

(57) ABSTRACT

The invention relates to a liquid crystal compound having the structure of formula I wherein R is selected from the group consisting of H and alkyl or alkoxy groups of 1 to 12 carbon atoms in which one or more H are unsubstituted or substituted with halogen; $A_1$ is selected from the group consisting of a single bond or a 1,4-phenylene group in which each H in the 1,4-phenylene group is independently substituted by one or more halogen atoms; $L_1$ and $L_2$ are each independently selected from H or halogen; $Z_1$ is a single bond or —$(CH_2)_2$—. The compound has advantages of low rotational viscosity, large dielectric anisotropy, good mutual solubility and stability, which can be added to LC composition to reduce the driving voltage of the display. Thus, the novel compound has prosperous applications in LCD industry.

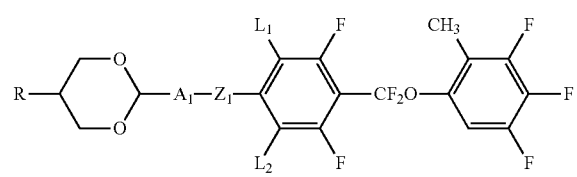

(I)

11 Claims, No Drawings

(56) References Cited

FOREIGN PATENT DOCUMENTS

| | | | |
|---|---|---|---|
| JP | 2014210935 A | | 11/2014 |
| KR | 10-2015-0053223 A | * | 4/2015 |
| TW | 201619107 A | | 6/2016 |
| TW | 201619357 A | | 6/2016 |
| TW | 201619358 A | | 6/2016 |
| WO | WO-2014063777 A1 | | 5/2014 |
| WO | WO-2016078389 A1 | | 5/2016 |
| WO | WO-2016082510 A1 | | 6/2016 |
| WO | WO-2016082511 A1 | | 6/2016 |

OTHER PUBLICATIONS

International Search Report (in English and Japanese) and Written Opinion of the International Searching Authority (in Japanese) issued in PCT/CN2015/080516, dated Aug. 20, 2015; ISA/CN.
International Search Report (in English and Japanese) and Written Opinion of the International Searching Authority (in Japanese) issued in PCT/CN2015/080517, dated Aug. 26, 2015; ISA/CN.

* cited by examiner

LIQUID CRYSTAL COMPOUND CONTAINING DIFLUOROMETHOXY BRIDGE, COMPOSITION AND APPLICATION THEREOF

CROSS REFERENCE TO RELATED APPLICATIONS

This application is a U.S. National Phase Application under 35 U.S.C. 371 of International Application No. PCT/CN2015/080515 filed on Jun. 1, 2015 and published in Chinese as WO 2016/082510 on Jun. 2, 2016. This application claims priority to Chinese Patent Application No. 201410707262.1 filed Nov. 27, 2014. The entire disclosures of all of the above applications are incorporated herein by reference.

FIELD OF THE INVENTION

The present invention relates to liquid crystal display materials, and more particularly to a liquid crystal compound containing a difluoromethoxy bridge, its compound and application thereof.

BACKGROUND OF THE INVENTION

As an environment-friendly material, liquid crystal molecule has significant research value and great potential applications in the field of information display, organic optoelectronics and so on. Liquid crystal as a novel display material has many advantages over other counterparts, such as low power consumption, low driving voltage. The state-of-the-art liquid crystal device is characterized by its small size, light weight, long life time, large information density, no electromagnetic radiation, etc., which can adapt to almost all kinds of information displays, especially in TFT-LCD products.

Currently, the TFT-LCD related technologies have been well established and successfully solved technical problems regarding viewing angle, resolution, color saturation and brightness. The display performances of TFT-LCDs are close to or superior to that of CRT displays. Large-screen and small-to-medium-screen TFT-LCD displays have gradually dominated the flat panel displays. However, due to the limitation of the liquid crystal material itself, TFT-LCD still has some defects, such as slow response, high driving voltage, low charge retention rate and so on. Therefore, it is particularly important to research a liquid crystal compound with low viscosity and high dielectric anisotropy.

A liquid crystal structure containing difluoromethoxy bridge and dioxane is illustrated in CN1182085A, assigned to Chiso, a Japanese company in 1998, but an ideal corresponding compound was not obtained.

SUMMARY OF THE INVENTION

In view of the above background, the present invention provides a novel liquid crystalline compound having a difluoromethoxy bridge structure. The compound is characterized by low rotational viscosity, large dielectric anisotropy, good mutual solubility and stability, which has the chemical structure as shown in formula I:

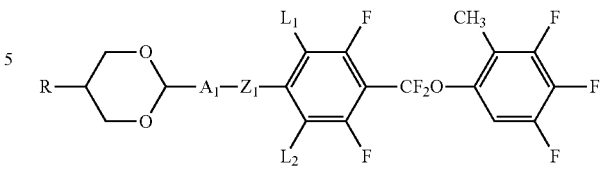

(I)

Wherein R is selected from the group consisting of H and alkyl or alkoxy having 1 to 12 carbon atoms in which one or more H is unsubstituted or substituted with halogen;

$A_1$ is selected from the group consisting of a single bond or a 1,4-phenylene group in which each H in the 1,4-phenylene group is independently substituted by one or more halogens;

$L_1$ and $L_2$ are each independently selected from H or halogen;

$Z_1$ is selected from the group consisting of a single bond or $-(CH_2)_2-$.

Preferably, the liquid crystal compound, according to the present invention, is of the structure, wherein:

R is selected from the group consisting of H and alkyl or alkoxy groups having 1-5 carbon atoms in which one or more H is unsubstituted or substituted with fluorine;

$A_1$ is selected from the group consisting of a single bond or a 1,4-phenylene group in which each H in the 1,4-phenylene group is independently substituted with one or more fluorine atoms;

$L_1$ and $L_2$ are each independently selected from H or F;

$Z_1$ is a single bond.

It is further preferred that:

R is selected from H and unsubstituted alkyl groups having 1 to 5 carbon atoms;

$A_1$ is selected from the group consisting of a single bond or a 1,4-phenylene group in which each H in the 1,4-phenylene group is independently substituted with one or more fluorine atoms;

$L_1$ and $L_2$ are all H;

$Z_1$ is a single bond.

And more preferably, the liquid crystalline compound is selected from the group consisting of the following general structural compounds:

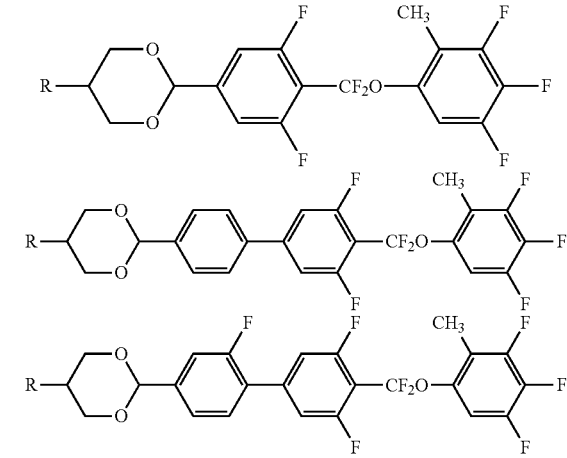

R is selected from alkyl groups containing from 1 to 5 carbon atoms;

As a preferred embodiment of the present invention, the liquid crystal compound is:

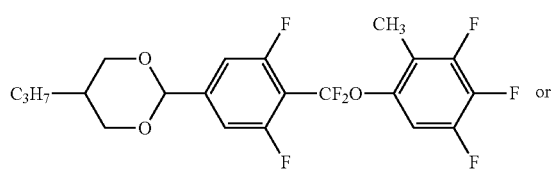

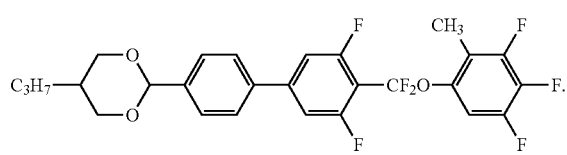

The above compounds have a high dielectric anisotropy and can be applied to the composition to reduce the driving voltage of the device.

A second object of the present invention is to provide a process for producing a difluoromethoxy bridge liquid crystal compound, which is prepared by the following route:

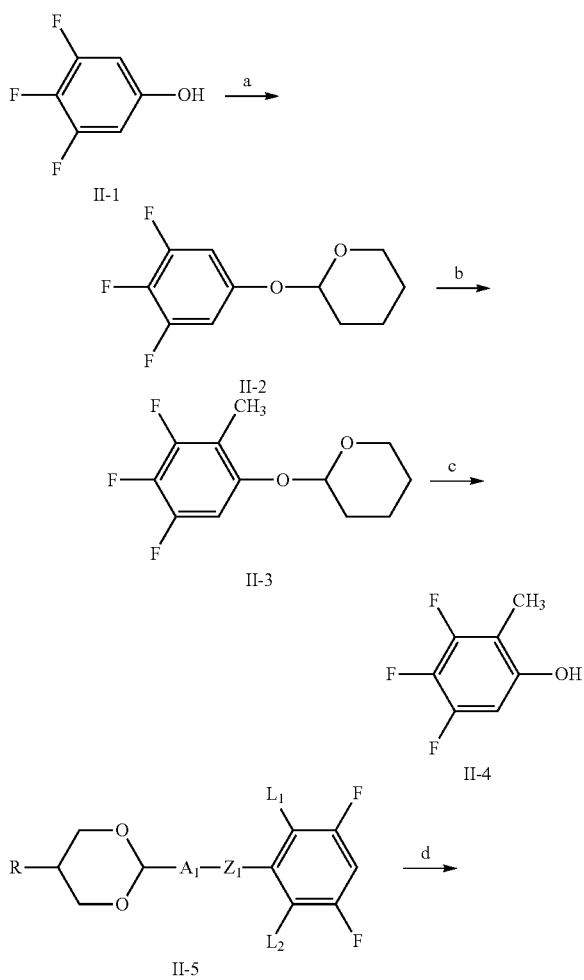

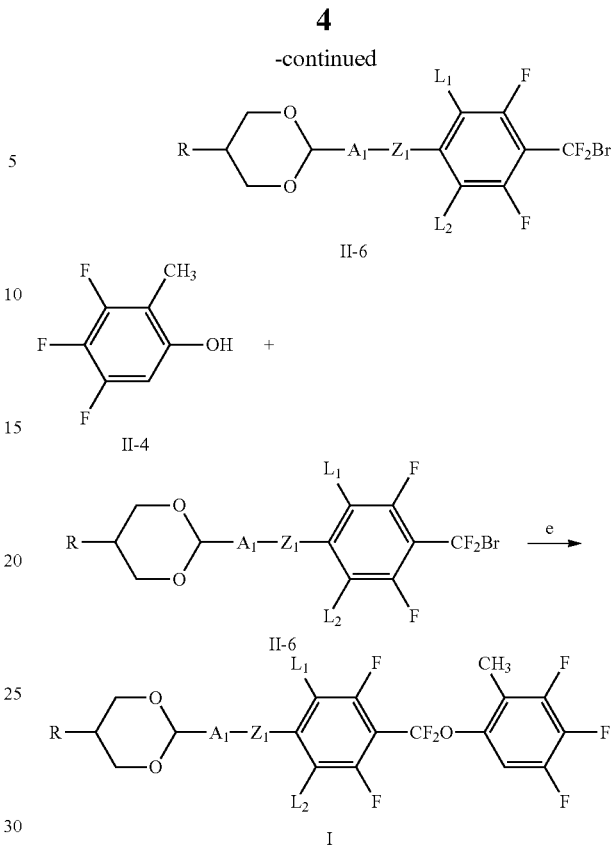

The synthesis comprises the following steps:

(a) Using compound II-1 as the starting material, with weak acid as catalyst and methylene chloride as solvent, reacting with dihydropyran at room temperature to obtain compound II-2;

(b) Compound II-2 was reacted with butyllithium in THF at −75° C. to −85° C. with tetrahydrofuran as a solvent to form a lithium reagent, and reacted with methyl iodide to obtain compound II-3;

(c) Compound II-3 was synthesized by the reaction of pyridinium p-toluenesulfonate as a catalyst under stirring and heating to obtain compound II-4.

(d) Compound II-5 was reacted with butyllithium at low temperature to form lithium reagent with tetrahydrofuran as solvent under nitrogen atmosphere, and reacted with difluorodibromomethane to obtain compound II-6.

(e) The reaction of compound II-4 and compound II-6 with dimethyl sulfoxide and water as solvent, tetrabutyl ammonium bromide as catalyst and potassium carbonate as acid-binding agent to yield the target compound I;

Wherein R, $A_1$, $Z_1$, $L_1$ and $L_2$ are as defined above.

The use of the above-mentioned production method enables batch stabilization to obtain a difluoromethoxy bridged liquid crystal compound, which has the advantage of large dielectric anisotropy.

In addition, the present invention also provides a liquid crystal composition containing a difluoromethoxy bridge-bond liquid crystal compound. Wherein the difluoromethoxy bridged liquid crystal compound is added in an amount of 1 to 80%, more preferably 3 to 50%, in a proper manner. The addition of the above-mentioned liquid crystal compound makes it possible to further improve the dielectric anisotropy of the conventional liquid crystal composition and to reduce the driving voltage of the device, as will be apparent to those skilled in the art.

Still another object of the present invention is to protect the above-mentioned liquid crystal compound containing difluoromethoxy bridge and its composition in the field of liquid crystal display.

Particularly the use of the compounds or compositions described above in liquid crystal display devices including but not limited to TN, ADS, FFS or IPS liquid crystal displays. The application of the liquid crystal composition to a liquid crystal display device has the advantage of lowering the driving voltage.

Abbreviations of performance testing parameters in the present invention are described as follows:

Δε represents dielectric anisotropy at 25° C. and 1 kHz;
γ1 represents rotational viscosity (mPa·s) at 25° C.;
Δn is optical anisotropy, $n_o$ is refractive index (589 nm, 25° C.);
C.p is clearing point of the liquid crystal composition (° C.);
VHR is voltage holding ratio (%), which is obtained by injecting a mixed liquid crystal into a liquid crystal cell and placing the liquid crystal cell into an incubator, performing the test program after the temperature being stable and manually taking points. The measurement voltage is 5V, the power-on time is 5 ms and the holding time is 500 ms.

DETAILED DESCRIPTION

Example 1

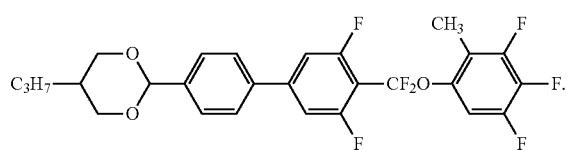

2-{4'-[(3,4,5-trifluoro-2-methyl-phenoxy)-difluoromethyl]-3',5'-difluorobiphenylene}-5-propyl-[1,3] Dioxane (Compound 7)

1) Synthesis of 2-(3,4,5-trifluoro-phenoxy)-tetrahydropyran (Compound 2)

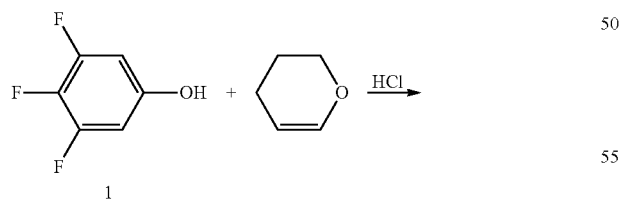

70 g of 3,4,5-trifluoro-phenol, 72 g of 2,3-dihydropyran, 140 ml of methylene chloride were added to a 500 ml three-necked flask with stirring, 5 drops of concentrated hydrochloric acid was dropwise added to the flask at room temperature. The reaction lasted for 3 hours at room temperature. The reaction solution was washed twice with 10% aqueous sodium hydroxide solution (100 ml×2), dried over anhydrous sodium sulfate (20 g) for 30 minutes and filtered out. The filtrate was evaporated to dryness.

2) Synthesis of 2-(3,4,5-trifluoro-2-methyl-phenoxy)-tetrahydropyran (Compound 3)

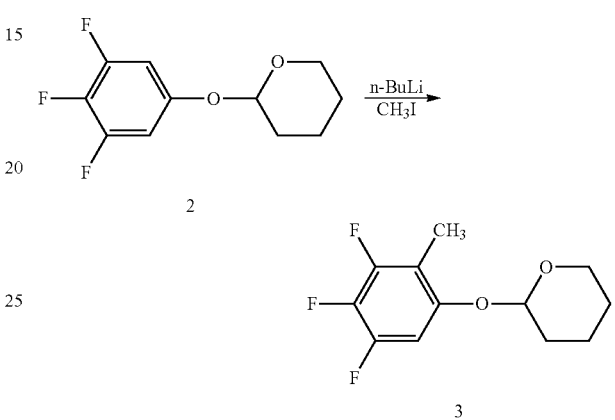

97 g of 2-(3,4,5-trifluoro-phenoxy)-tetrahydropyran (Compound 2) and 500 ml tetrahydrofuran were added into a 1 L dried and clean three-necked flask, protected under nitrogen, cooled to −75° C. to −85° C. by using liquid nitrogen, added dropwise with 200 ml butyllithium, reacted for 1 hour under a control of temperature after the completion of dropwise addition, added dropwise with 89 g methyl iodide, reacted for 30 minutes at a temperature controlled at −75° C. to −85° C. after the completion of dropwise addition, and then the temperature was naturally raised to −20° C., the reaction solution was hydrolyzed and destroyed with an aqueous ammonium chloride solution. Liquid separation was performed, the aqueous phase was extracted twice with 100 ml ethyl acetate, the organic phases were combined, washed twice with 100 ml aqueous sodium chloride solution, dried with 30 g anhydrous sodium sulfate for 30 minutes and subjected to suction filtration, and the filtrate is spin-dried and crystallized with 1.5 times of ethanol to obtain a white solid.

Theoretical yield: 102 g, actual yield: 64 g, yield: 62.7%, white solid, GC: 99.6%, melting point: 67.65 C.

3) Synthesis of 3,4,5-trifluoro-2-methyl-phenol (Compound 4)

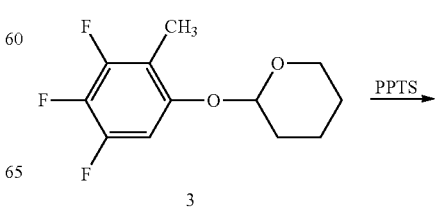

-continued

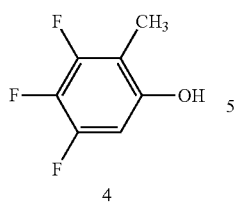
4

10 g of 2-(3,4,5-trifluoro-2-methyl-phenoxy)-tetrahydropyran (Compound 3), 2 g of pyridinium p-toluenesulfonate and 50 ml of ethanol were added into a 100 ml dried and clean three-necked flask, stirred and heated to 60° C.-70° C., and reacted for 3 hours in a timing manner. The reaction solution was spin-dried, added with 20 ml dichloromethane to dissolve the product, washed twice with 10 ml aqueous sodium chloride solution and dried with 10 g anhydrous sodium sulfate for several minutes and spin-dried.

The theoretical yield: 6.5 g, the actual yield: 6.5 g, yield: 100% (according to theory), colorless liquid, GC: 99.155%.

4) Synthesis of difluoromethyl bromide (Compound 6)

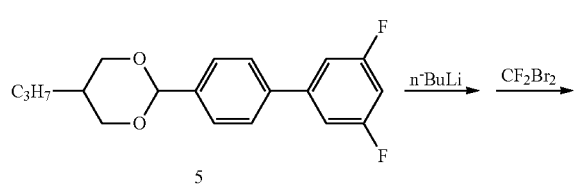

141.5 g of 2-(3',5'-difluorobiphenylene)-5-propyl-[1,3] dioxane (Compound 5) and 1 L of tetrahydrofuran were added into 2 L three-necked flask, stirred until the solid was completely dissolved, purged nitrogen three times, cooled to −70☐, added dropwise with 232 ml 2.5M butyl lithium at −65~−75° C. Once the dropping completed, the dropping funnel was rinsed with 100 ml tetrahydrofuran. The reaction lasted one hour at temperature −65~−75° C., then added dropwise tetrahydrofuran 0.5 L solution containing 141 g of difluorodibromomethane at −65~−75° C. When dropping was completed, the temperature was raised naturally up to −20° C.

A solution of 40 ml of concentrated hydrochloric acid and 200 ml of water was added dropwise to the reaction solution. After stirring for 30 minutes, the aqueous phase was separated by standing. 0.5 L of petroleum ether was added and the mixture was washed three times with 1 L water. The product was a yellow liquid with a weight of 190 g and a yield of 95%.

2-{4'-[(3,4,5-trifluoro-2-methyl-phenoxy)-difluoromethyl]-3',5'-difluorobiphenylene}-5-propyl-[1,3]Dioxane (Compound 7)

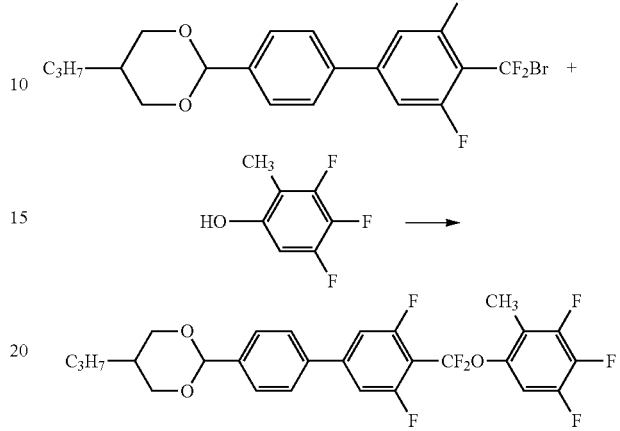

2 L three-necked flask was charged with 190 g of difluoromethyl bromide (Compound 6), 1 L of dimethylsulfoxide and 0.2 L of water and stirred. 72 g of 3,4,5-trifluoro-2-methylphenol (Compound 4), 14 g tetrabutylammonium bromide, 123 g potassium carbonate were also added to the flask while stirring, purging nitrogen three times. The reaction lasted for 5 hours at temperature 90~95° C.

After the reaction output was suction-filtrated, its filter cake was extracted by hot toluene 400 ml. The solution was filtrated again and the filter cake was washed by toluene. The filtrates were combined and washed four times with sodium chloride aqueous solution and then spin-dried off the solvent. The reaction product was recrystallized by 1-fold of petroleum ether and 2-fold of anhydrous ethanol. Then recrystallizations were carried out with 2-fold of ethanol and 1-fold of toluene for 3 times. The final white solid product was turned out by suction-filtration.

Product Analysis:
Gas purity (GC) 99.9%
Melting point: 114.4° C.,
Clear point: 128.3° C.,
$\Delta n$ is 0.137,
$\Delta \varepsilon$ is 33.7,
$\gamma 1$ is 202 mPa·s.
Mass spectrometry fragment: 239, 267, 367, 528 (molecular ion peak);
H-NMR Nuclear Magnetic Spectrum (CDCl3, 300 MHz): δH: 0.90-2.60 (m, 11H), 3.70-4.10 (m, 4H), 5.98 (m, 1H), 6.10-7.60 (m, 7H). Gas chromatographic (GC) purity is 99.9%, Example 2

2-{4-[(3,4,5-trifluoro-2-methyl-phenoxy)-difluoromethyl]-3,5-difluorobenzene}-5-propyl-[1,3] Dioxane (Compound 10)

(Compound 8 in this Example can be obtained by referring to Step 1-3 disclosed in Example 1, and will not be repeated here)

1) Synthesis of Difluoromethyl Bromide (Compound 9)

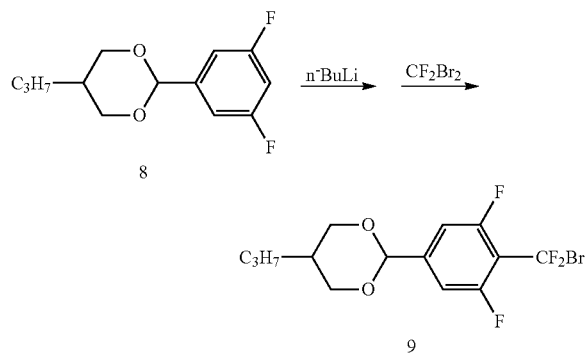

108 g of 2-(3',5'-difluorobiphenylene)-5-propyl-[1,3] dioxane (Compound 5) and 1 L of tetrahydrofuran were added into 2 L three-necked flask, stirred until the solid was completely dissolved, and purged nitrogen three times, cooled to −70□, added dropwise 232 ml 2.5M butyl lithium at −65~−75° C. Once the dropping completed, the dropping funnel was rinsed with 100 ml tetrahydrofuran. The reaction lasted one hour at temperature −65~−75° C., then added dropwise tetrahydrofuran 0.5 L solution containing 141 g of difluorodibromomethane at −65~−75° C. When dropping was completed, the temperature was raised naturally up to −20° C.

A solution of 40 ml of concentrated hydrochloric acid and 200 ml of water was added dropwise to the reaction solution. After stirring for 30 minutes, the aqueous phase was separated by standing. 0.5 L of petroleum ether was added and the mixture was washed three times with water (1 L×3). After spin-evaporated, the product was a yellow liquid with a weight of 157 g and a yield of 95%.

2) Synthesis of 2-{4-[(3,4,5-trifluoro-2-methyl-phenoxy)-difluoromethyl]-3,5-difluorobenzene}-5-propyl-[1,3] Dioxane (Compound 10)

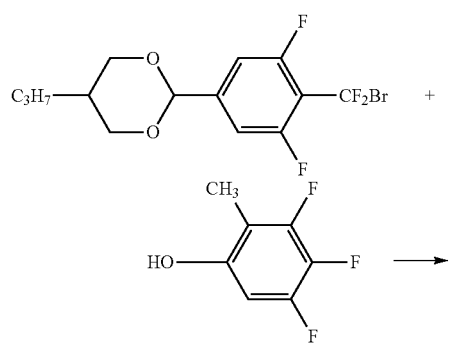

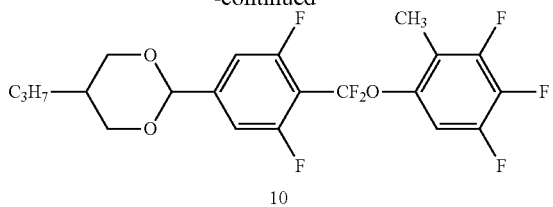

157 g of difluoromethyl bromide (Compound 6), 1 L of dimethylsulfoxide and 0.2 L of water were added into 2 L three-necked flask and stirred. 72 g of 3,4,5-trifluoro-2-methylphenol (Compound 4), 14 g tetrabutylammonium bromide, 123 g potassium carbonate were also added to the flask while stirring, followed by purging nitrogen three times. The reaction lasted for 5 hours at 90~95° C.

After the reaction liquid was suction-filtrated, its filter cake was extracted with hot toluene 400 ml. The solution was filtrated again and the resultant filter cake was washed by toluene. The filtrates were combined and washed four times with sodium chloride aqueous solution and then spin-dried off the solvent. The reaction product was recrystallized by 1-fold of petroleum ether and 2-fold of anhydrous ethanol. Then recrystallizations were carried out with 2-fold of ethanol and 1-fold of toluene for three times. The final white solid product was turned out by suction-filtration and air-dried. The theoretical yield: 191.5 g, the actual yield: 70.0 g, yield 36.5%.

Product Analysis:
Gas purity (GC) 99.9%
Δn is 0.068,
Δε is 28.5,
γ1 is 57 mPa·s.
Mass spectrometry fragment: 163, 191, 291, 452 (molecular ion peak);
H-NMR Spectrum (CDCl3, 300 MHz): δH: 0.90-2.60 (m, 11H), 3.70-4.10 (m, 4H), 5.98 (m, 1H), 6.10-7.60

Example 3-12

According to the technical scheme of Examples 1-2, the following compounds can be synthesized by simply replacing the starting material containing the corresponding groups:

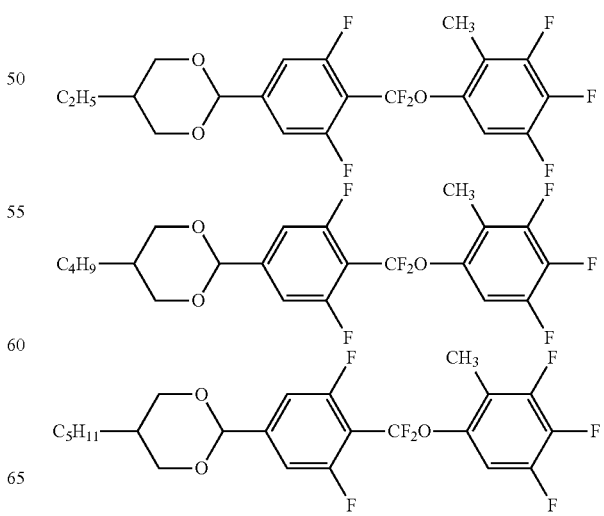

-continued

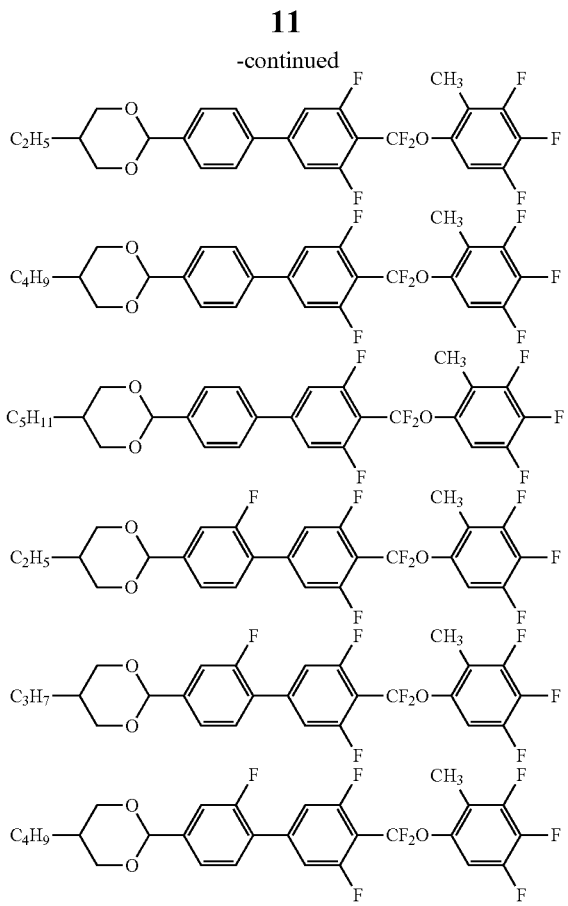

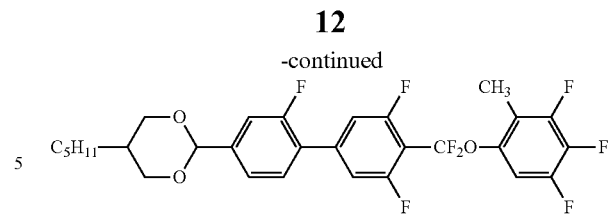

Example 13: Mixed Liquid Crystal Composition

All of the liquid crystal monomers used in the following compositions were supplied by Beijing Billion Space-Time Liquid Crystal Technology Co., The contents of the components in the examples represent mass percentages unless otherwise specified.

The following parts by weight of the liquid crystal compound were prepared to form a liquid crystal composition. The specific formulation and the performance parameters of the resultant liquid crystal composition are shown in the following table.

The application examples of liquid crystal compounds having a difluoromethyl ether bridge structure in TN, IPS, FFS, and ADS-TFT modes are shown in Tables 1 and 2, respectively. Meanwhile, in order to verify the performance of the liquid crystal compound of the present invention, a performance comparison was made between the liquid crystal composition formed by adding the above-mentioned compound and the conventional dielectric anisotropic compound. The results are shown in Tables 1 to 4.

TABLE 1

Parts by weight percentage and performance parameters of the liquid crystal composition

| Components | Parts | Parameters | |
|---|---|---|---|
| 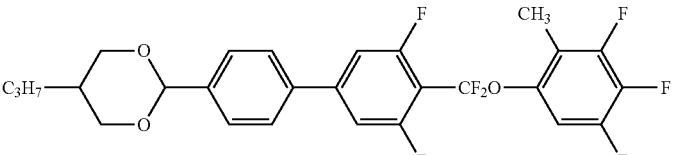 (compound 7) | 10 | Δn | 0.095 |
| 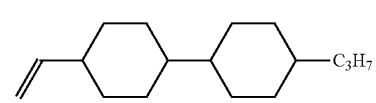 | 22.5 | Δε | 8.52 |
| 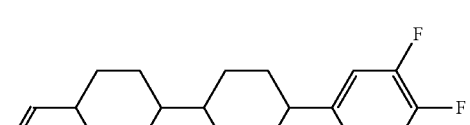 | 22.5 | γ1 | 84.6 |
| 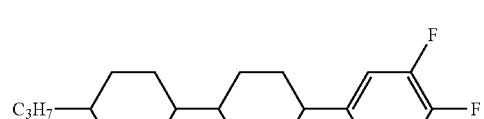 | 18 | C.p (° C.) | 82.3 |

TABLE 1-continued

Parts by weight percentage and performance parameters of the liquid crystal composition

| Components | Parts | Parameters | |
|---|---|---|---|
| C₃H₇–⟨cyclohexyl⟩–⟨phenyl⟩–⟨phenyl(3,4,5-triF)⟩ | 13.5 | VHR (%) | 99.5 |
| C₅H₁₁–⟨cyclohexyl⟩–⟨phenyl⟩–⟨phenyl(3,4,5-triF)⟩ | 13.5 | | |

TABLE 2

Parts by weight of each component and performance parameters of the liquid crystal composition

| Components | Parts | Parameters | |
|---|---|---|---|
| C₃H₇–⟨dioxane⟩–⟨phenyl(2,6-diF)⟩–CF₂O–⟨phenyl(2-CH₃,3,5-diF)⟩–F (compound 10) | 10 | Δn | 0.087 |
| CH₂=CH–⟨cyclohexyl⟩–⟨cyclohexyl⟩–C₃H₇ | 22.5 | Δε | 8.00 |
| CH₂=CH–⟨cyclohexyl⟩–⟨cyclohexyl⟩–⟨phenyl(3,4-diF)⟩ | 22.5 | γ1 | 70.1 |
| C₃H₇–⟨cyclohexyl⟩–⟨cyclohexyl⟩–⟨phenyl(3,4-diF)⟩ | 18 | C.p (° C.) | 68.9 |
| C₃H₇–⟨cyclohexyl⟩–⟨phenyl⟩–⟨phenyl(3,4,5-triF)⟩ | 13.5 | VHR (%) | 99.5 |
| C₅H₁₁–⟨cyclohexyl⟩–⟨phenyl⟩–⟨phenyl(3,4,5-triF)⟩ | 13.5 | | |

TABLE 3
Performance parameters of the liquid crystal composition without the addition of the compound of the invention
| Components | Parts | Parameters | |
|---|---|---|---|
| 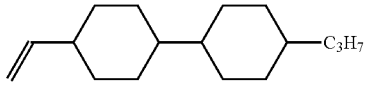 | 25 | Δn | 0.090 |
| 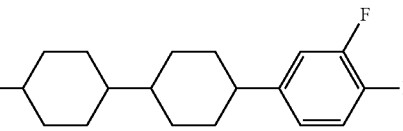 | 25 | Δε | 4.86 |
| 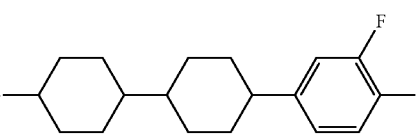 | 20 | γ1 | 83.4 |
| 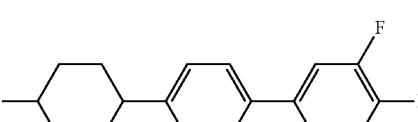 | 15 | C.p (° C.) | 79.1 |
| 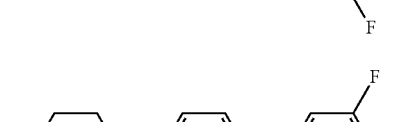 | 15 | VHR (%) | 99.5 |
TABLE 4
Control sample of the weight parts and the performance parameters of the respective components in the liquid crystal composition
| Components | Parts | Parameters | |
|---|---|---|---|
| 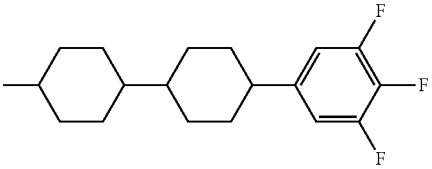 | 10 | Δn | 0.095 |
| 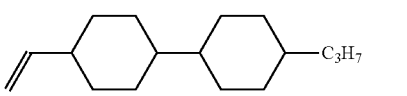 | 22.5 | Δε | 6.05 |
| 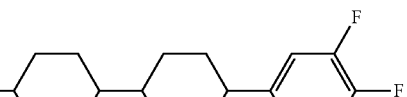 | 22.5 | γ1 | 82.1 |
| 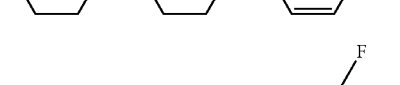 | 18 | C.p (° C.) | 80.5 |

TABLE 4-continued

Control sample of the weight parts and the performance parameters of the respective components in the liquid crystal composition

| Components | Parts | Parameters | |
|---|---|---|---|
| 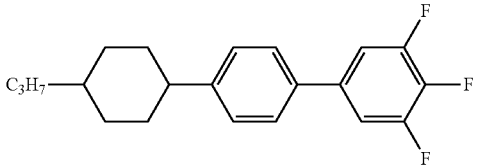 | 13.5 | VHR (%) | 99.5 |
| 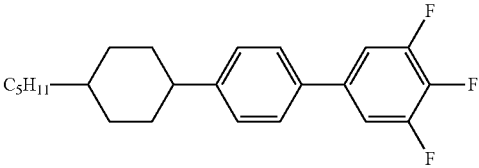 | 13.5 | | |

As apparent from Tables 1 to 4, the liquid crystal composition in which the compound of the present invention is directly added or the compound of the present invention have been used in place of the conventional dielectric anisotropic compound (compound 11) has moderate rotational viscosity, moderate Δn value, high charge retention rate, in particular, has a large dielectric anisotropy. Meanwhile, the liquid crystal composition of the present invention consists of the above-mentioned compound in an amount of 1 to 80%, more preferably 3 to 50%.

In addition to the composition exemplified in the Examples, other liquid crystal compositions to which the liquid crystal compounds having a difluoromethyl ether bridge-bond structure provided by the present invention can also render the same excellent optical and electrical properties.

While the invention has been described in detail and with reference to the following general description, detailed description, and testing, it will be obvious to those skilled in the art that modifications and improvements may be made thereto without departing from the invention. Accordingly, it is intended that the present invention cover the modifications and variations of this invention without departing from the spirit of the invention.

What is claimed is:

1. A liquid crystal compound comprising difluoromethoxy bridge structure as shown by formula I:

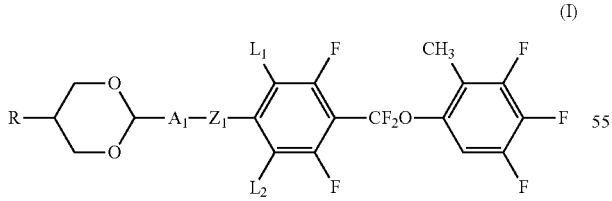

(I)

wherein R is selected from the group consisting of H and alkyl or alkoxy having 1 to 12 carbon atoms in which one or more H is unsubstituted or substituted with halogen;

$A_1$ is selected from the group consisting of a single bond or a 1,4-phenylene group in which each H in the 1,4-phenylene group is independently substituted by one or more halogens;

$L_1$ and $L_2$ are each independently selected from H or halogen;

$Z_1$ is selected from the group consisting of a single bond or —$(CH_2)_2$—.

2. The liquid crystal compound according to claim 1, wherein the compound is characterized in that R is selected from the group consisting of H and alkyl or alkoxy groups having 1-5 carbon atoms in which one or more H is unsubstituted or substituted with fluorine;

$A_1$ is selected from the group consisting of a single bond or a 1,4-phenylene group in which each H in the 1,4-phenylene group is independently substituted with one or more fluorine atoms;

$L_1$ and $L_2$ are each independently selected from H or F;

$Z_1$ is a single bond.

3. The liquid crystal compound according to claim 1, wherein the compound is characterized in that R is selected from H and unsubstituted alkyl groups having 1 to 5 carbon atoms;

$A_1$ is selected from the group consisting of a single bond or a 1,4-phenylene group in which each H in the 1,4-phenylene group is independently substituted with one or more fluorine atoms;

$L_1$ and $L_2$ are all H;

$Z_1$ is a single bond.

4. The liquid crystal compound according to claim 1, wherein the compound is characterized in that the liquid crystal compound having structures represented by the following general formulas:

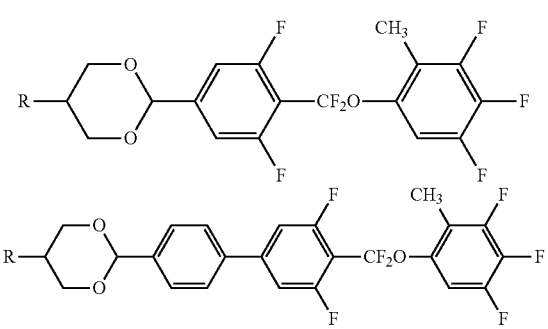

-continued

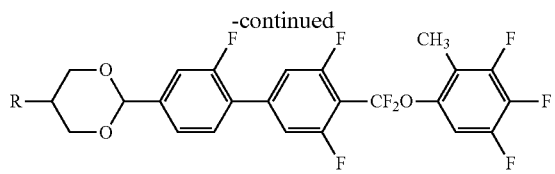

R is selected from alkyl groups containing from 1 to 5 carbon atoms.

5. The liquid crystal compound according to claim 1, wherein the compound is characterized in that the liquid crystal compound having structures represented by the following general formulas:

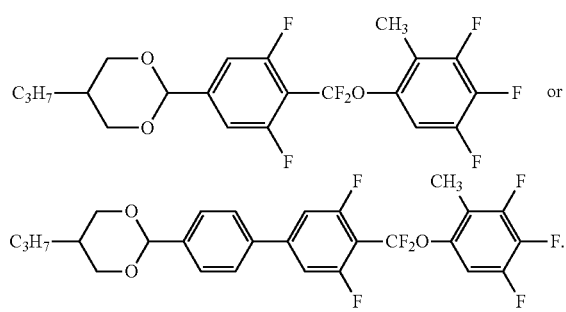

6. A liquid crystal composition containing the liquid crystal compound according to claim 1.

7. A liquid crystal composition according to claim 6, wherein the composition is characterized in that the percentage of the liquid crystal compound is in the range of 1-80%.

8. A liquid crystal composition according to claim 6, wherein the composition is characterized in that the percentage of the liquid crystal compound is in the range of 3-50%.

9. The liquid crystal compound according to claim 1, wherein the liquid crystal compound is for liquid crystal displays.

10. The liquid crystal compound according to claim 4, wherein the liquid crystal compound includes structures represented by the following general formulas:

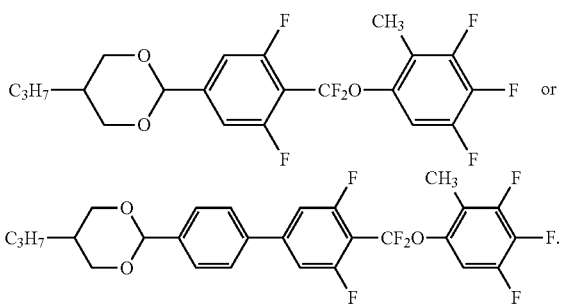

11. The liquid crystal composition according to claim 6, wherein the liquid crystal composition is for liquid crystal displays.

* * * * *